US006893838B1

(12) United States Patent
Telliez et al.

(10) Patent No.: US 6,893,838 B1
(45) Date of Patent: May 17, 2005

(54) DADD, DEATH ACTIVATOR DEATH DOMAIN PROTEIN

(75) Inventors: Jean-Baptiste Telliez, Waltham, MA (US); Lih-Ling Lin, Concord, MA (US)

(73) Assignee: Genetics Institute LLC, Cambridge, MA (US)

(*) Notice: Subject to any disclaimer, the term of this patent is extended or adjusted under 35 U.S.C. 154(b) by 0 days.

(21) Appl. No.: 09/056,383

(22) Filed: Apr. 7, 1998

(51) Int. Cl.$^7$ .................. C12N 15/00; C12N 15/63; C12N 5/16; C12N 1/21; C07H 21/04

(52) U.S. Cl. .................. 435/69.1; 435/320.1; 435/325; 435/254.11; 536/23.1; 536/23.5

(58) Field of Search .................. 435/69.1, 320.1, 435/325, 252.3, 254.11; 536/23.5, 23.1

(56) References Cited

U.S. PATENT DOCUMENTS

| | | | |
|---|---|---|---|
| 4,235,871 A | 11/1980 | Papahadjopoulos et al. | 424/19 |
| 4,501,728 A | 2/1985 | Geho et al. | 424/38 |
| 4,518,584 A | 5/1985 | Mark et al. | 424/85 |
| 4,737,323 A | 4/1988 | Martin et al. | 264/4.3 |
| 4,837,028 A | 6/1989 | Allen | 424/450 |
| 5,296,592 A | 3/1994 | Dower et al. | 530/413 |
| 5,464,764 A | 11/1995 | Capecchi et al. | 435/172.3 |
| 5,487,992 A | 1/1996 | Capecchi et al. | 435/172.3 |
| 5,614,396 A | 3/1997 | Bradley et al. | 435/172.3 |
| 5,616,491 A | 4/1997 | Mak et al. | 435/354 |
| 5,627,059 A | 5/1997 | Capecchi et al. | 435/172.3 |
| 5,631,153 A | 5/1997 | Capecchi et al. | 435/172.3 |
| 5,679,523 A | 10/1997 | Li et al. | 435/6 |

FOREIGN PATENT DOCUMENTS

| | | |
|---|---|---|
| EP | 308378 | 3/1989 |
| EP | 393438 | 10/1990 |
| EP | 433900 | 6/1991 |
| EP | 526905 | 2/1993 |
| EP | 568925 | 11/1993 |
| EP | 649464 | 4/1995 |
| WO | WO 91/03553 | 3/1991 |
| WO | WO 93/19777 | 10/1993 |
| WO | WO 96/36730 | 11/1996 |

OTHER PUBLICATIONS

US 5,843,791, 12/1998, Hauptmann et al. (withdrawn)
Houdebine, Journal of Biotechnology, 1994, vol. 34, pp. 269–287.*
Verma et al (Nature, 1997, vol. 389, pp. 239–242).*
Eck et al (Gene–Based Therapy, In: The Pharmacological Basis of Therapeutics, Goodman and Gilman, Ed.s, 1996, pp. 77–101).*
Orkin et al ("Report and Recommendation of the Panel to Assess the NIH Investment in Research on Gene Therapy", NIH, 1995).*
Lehningen "Biochemistry" 1975 p. 962, Worth Publishers, Inc, New York, NY.*
Current Protocols in Molecular Biology 1990, ed—Ausubel et al p. 16.7.1–16.7.8.*
Genbank Accession No: AA507436 (Aug. 18, 1997).*
Genbank Accession No: AA631067 (Oct. 31, 1997).*
Genbank Accession No. N39432 (Jan. 19, 1996).*
Genbank Accession No. N55392 (Feb. 20, 1996).*
Genbank Accession No. N50632 (Feb. 14, 1996).*
Genbank Accession No. R13288 (Apr. 12, 1995).*
Genbank Accession No. AA118566 (Nov. 19, 1996).*
Genbank Accession No. AA714504 (Dec. 29, 1997).*
Genbank Accession No. AA642327 (Nov. 13, 1997).*
Albert, Paul R. and Morris, Stephen J. "Antisense knockouts: molecular scalpets for the dissection of signal transduction" *Trends Pharmacol. Sci.* 15(7):250–54 (1994).
Chinnaiyan, Arul M. et al. "FADD, a Novel Death Domain–Containing Protein, Interacts with the Death Domain of Fas and Initiates Apoptosis" *Cell* 81:505–12 (May 19, 1995).
Chinnaiyan, Arul M. et al, "Signal Transduction by DR3, a Death Domain–Containing Receptor Related to TNFR–1 and CD95" *Science* 274:990–92 (Nov. 8, 1996).
Clark, Andrew G. et al, "Nature screen: An efficient method for screening natural populations of *Drosophilia* for targeted P–element insertions" *Proc. Natl. Acad. Sci. USA* 91(2):719–22 (Jan. 1994).
Genbank Accession No. AA631067 for nq77c12.s1 NCI_CGAP_Pr22 Homo sapiens cDNA clone IMAGE:1158358 3', mRNA sequence.
Genbank Database Accession No. A1022161 for ow68g09.x1 Soares_fetal_liver_spleen_1NFLS_S1 Homo sapiens cDNA clone IMAGE:1652032 3', mRNA sequence.
Hampel, Arnold : The Halrpin Ribozyme: Discovery, Two–Dimensional Model, and Development for Gene Therapy *Prog. Nucleic Acid Res. Mol. Biol.* 58:1–39 (1998).
Hsu, Hailing et al., "The TNF Receptor 1–Associated Protein TRADD Signals Cell Death and NF–kB Activation" *Cell* 81:495–504 (May 19, 1995).
Lavrovsky, Yan et al. "Therapeutic Potential and Mechanism of Action of Oligonucleotides and Ribozomes" *Biochem. Mol. Med.* 62(1):11–22 (1997).
Mansour, Suzanne L. et al. "Disruption of the proto–oncogene *int–2* in mouse embryo–derived stem cells: a general strategy for targeting mutations to non–selectable genes" *Nature* 336:348–52 (Nov. 24, 1988).
Pan, Guohua et al. "The Receptor for the Cylotoxic Ligand TRAIL" *Science* 276:111–13 (Apr. 4, 1997).
Plasterk, Ronald H.A. "Reverse Genetics of *Caenorhabditis elegans*" *Bioessays* 14(9):629–33 (Sep. 1992).

(Continued)

*Primary Examiner*—Karen A. Canella
(74) *Attorney, Agent, or Firm*—Ivor R. Elrifi; David E. Johnson; Mintz Levin

(57) ABSTRACT

Polynucleotides encoding DADD protein are also disclosed, along with vectors, host cells, and methods of making DADD protein. Methods of identifying inhibitors of DADD death domain binding and inhibitors identified by such methods are also disclosed.

14 Claims, No Drawings

OTHER PUBLICATIONS

Schall, Thomas J. et al. "Molecular Cloning and Expression of a Receptor for Human Tumor Necrosis Factor" *Cell* 61:361–370 (Apr. 20,1990).

Schievelia, Andrea R. et al. "MADD, a Novel Death Domain Protein That Interacts with the Type 1 Tumor Necrosis Factor Receptor and Activates Mitogen–activated Protein Kinase" *J. Biol. Chem.* 272(18):12063–75 (1997).

Stanger, Ben Z. et al. "RIP: A Novel Protein Containing a Death Domain That Interacts with Fas/APO–1 (CD95) in Yeast and Causes Cell Death" *Cell* 81:513–23 (May 19, 1995).

Tartaglia, Louis A. et al. "A Novel Domain within the 55 kd TNF Receptor Signals Cell Death" *Cell* 74:845–53 (Sep. 10, 1993).

Zwaal, Richard R. et al. "Target–selected gene inactivation in *Caenorhabditis elegans* by using a frozen transposon insertion mutant bank" *Proc. Natl. Acad. Sci. USA* 90(16):7431–35 (Aug. 1993).

\* cited by examiner

DADD, DEATH ACTIVATOR DEATH DOMAIN PROTEIN

BACKGROUND OF THE INVENTION

Tumor necrosis factor (herein "TNF") is a cytokine which produces a wide range of cellular activities. TNF causes an inflammatory response, which can be beneficial, such as in mounting an immune response to a pathogen, or when overexpressed can lead to other detrimental effects of inflammation.

The cellular effects of TNF are initiated by the binding of TNF to its receptors (TNF-Rs) on the surface of target cells. The isolation of polynucleotides encoding TNF-Rs and variant forms of such receptors has been described in European patent publication Nos. EP 308,378, EP 393,438, EP 433,900, EP 526,905 and EP 568,925; in PCT patent publication Nos. WO91/03553 and WO93/19777; and by Schall et al., Cell 61:361–370 (1990) (disclosing the P55 type TNF receptor). Processes for purification of TNF-Rs have also been disclosed in U.S. Pat. No. 5,296,592.

Native TNF-Rs are characterized by distinct extracellular, transmembrane and intracellular domains. The primary purpose of the extracellular domain is to present a binding site for TNF on the outside of the cell. When TNF is bound to the binding site, a "signal" is transmitted to the inside of the cell through the transmembrane and intracellular domains, indicating that binding has occurred. Transmission or "transduction" of the signal to the inside of the cell occurs by a change in conformation of the transmembrane and/or intracellular domains of the receptor. This signal is "received" by the binding of proteins and other molecules to the intracellular domain of the receptor, resulting in the effects seen upon TNF stimulation. Two distinct TNF receptors of −55 kd ("TNF-R1") and −75 kd ("TNF-R2") have been identified. Numerous studies with anti-TNF receptor antibodies have demonstrated that TNT-R1 is the receptor which signals the majority of the pleiotropic activities of TNF.

The domain required for signaling cytotoxicity and other TNF-mediated responses has been mapped to the −80 amino acid near the C-terminus of TNF-R1. This domain is therefore termed the "death domain" (hereinafter referred to as "TNF-R death domain") (see, Tartaglia et al., Cell 74:845–853 (1993)). Other proteins have been identified which also have regions homologous to the TNF-R death domain. These regions are also referred to generically as "death domains." Examples of proteins having such a death domain include Fas (Tartaglia et al., Cell 74: 845–853 (1993)), FADD (Chinnaiyan et al., Cell 81: 505–512 (1995)), RIP (Stanger et al., Cell 81: 513–523 (1995)), TRADD (Hsu et al., Cell 81: 495–504 (1995)), DR3 (Chinnaiyan et al., Science 274: 990–992 (1996)), and DR4 (Pan et al., Science, 276: 111–113 (1997)).

One activity produced by the interaction of TNF with TNF-R is cell death or apoptosis. It has been determined that the cell death process is mediated by the interaction of the death domains of TNF-R and other death domain-containing proteins. After binding of TNF to TNF-R, such proteins associate, forming homodimer and heterodimers, resulting in the instigation of the apoptotic process. As a result, inhibiting the interaction of death domain proteins will inhibit the induction of apoptosis.

It would, therefore, be desireable to identify new death domain-containing proteins which may be involved in the apoptotic process in order to in turn identify inhibitors of death domain associations and the apoptotic process resulting therefrom.

SUMMARY OF THE INVENTION

Applicants have for the first time identified novel DADD proteins and have isolated polynucleotides encoding such proteins.

In one embodiment, the present invention provides a composition comprising an isolated polynucleotide encoding a protein having DADD protein activity. In preferred embodiments, the polynucleotide is selected from the group consisting of:

(a) a polynucleotide comprising the nucleotide sequence of SEQ ID NO:12;

(b) a polynucleotide comprising the nucleotide sequence of SEQ ID NO:12 from nucleotide 794 to nucleotide 3052;

(c) a polynucleotide comprising the nucleotide sequence of SEQ ID NO:12 from nucleotide 1295 to nucleotide 3052;

(d) a polynucleotide comprising the nucleotide sequence of SEQ ID NO:12 from nucleotide 2726 to nucleotide 2929;

(e) a polynucleotide comprising a fragment of the nucleotide sequence of SEQ ID NO:12;

(f) a polynucleotide encoding a DADD protein comprising the amino acid sequence of SEQ ID NO:13;

(g) a polynucleotide encoding a DADD protein comprising the amino acid sequence of SEQ ID NO:13 from amino acid 167 to amino acid 753;

(h) a polynucleotide encoding a DADD protein comprising the amino acid sequence of SEQ ID NO: 13 from amino acid 645 to amino acid 712;

(i) a polynucleotide encoding a DADD protein comprising a fragment of the amino acid sequence of SEQ ID NO:13; and (j) a polynucleotide capable of hybridizing under stringent conditions to any one of the polynucleotides specified in (a)–(i).

In certain preferred embodiments, the polynucleotide is operably linked to an expression control sequence. The invention also provides a host cell, including bacterial, yeast, insect and mammalian cells, transformed with such polynucleotide compositions.

Processes are also provided for producing a DADD protein, which comprises:

(a) growing a culture of the host cell transformed with such polynucleotide compositions in a suitable culture medium; and (b) purifying the DADD protein from the culture.

The protein produced according to such methods is also provided by the present invention.

Compositions comprising a protein having DADD protein activity are also disclosed. In preferred embodiments the protein comprises an amino acid sequence selected from the group consisting of:

(a) the amino acid sequence of SEQ ID NO:13;

(b) the amino acid sequence of SEQ ID NO:13 from amino acid 167 to amino acid 753;

(c) the amino acid sequence of SEQ ID NO:13 from amino acid 645 to amino acid 712; and (d) fragments of the amino acid sequence of SEQ ID NO:13;

the protein being substantially free from other mammalian proteins. Such compositions may further comprise a pharmaceutically acceptable carrier.

Compositions comprising an antibody which specifically reacts with such DADD protein are also provided by the present invention.

Methods are also provided for identifying an inhibitor of binding of a DADD protein to a second protein having a death domain which comprise:

(a) combining said DADD protein with said second protein, said combination forming a first binding mixture;

(b) measuring the amount of binding between the DADD protein and the second protein in the first binding mixture;

(c) combining a compound with the DADD protein and the second protein to form a second binding mixture;

(d) measuring the amount of binding between the DADD protein and the second protein in the second binding mixture; and (e) comparing the amount of binding in the first binding mixture with the amount of binding in the second binding mixture;

wherein the compound is capable of inhibiting binding when a decrease in the amount of binding occurs in the second mixture as compared to the first mixture. In certain preferred embodiments the second protein is either a protein comprising the death domain of TNF-R or a DADD protein. In other preferred embodiments, the DADD protein used in such method comprises an amino acid sequence selected from the group consisting of:

(a) the amino acid sequence of SEQ ID NO:13;
(b) the amino acid sequence of SEQ ID NO:13 from amino acid 167 to amino acid 753;
(c) the amino acid sequence of SEQ ID NO:13 from amino acid 645 to amino acid 712; and
(d) fragments of the amino acid sequence of SEQ ID NO:13;

Compositions comprising inhibitors identified according to such method are also provided. Such compositions may include pharmaceutically acceptable carriers.

Methods are also provided for preventing or ameliorating an inflammatory condition which comprises administering a therapeutically effective amount of a composition comprising a protein having DADD protein activity and a pharmaceutically acceptable carrier.

Other embodiments provide methods of inhibiting TNF-R death domain binding comprising administering a therapeutically effective amount of a composition comprising a protein having DADD protein activity and a pharmaceutically acceptable carrier.

Methods of preventing or ameliorating an inflammatory condition or of inhibiting DADD death domain binding are provided, which comprise administering to a mammalian subject a therapeutically effective amount of inhibitors of DADD death domain binding, are also provided.

Methods of identifying an inhibitor of DADD death domain binding are also provided by the present invention which comprise:

(a) transforming a cell with a first polynucleotide encoding a DADD protein, a second polynucleotide encoding a second protein having a death domain, and at least one reporter gene, wherein the expression of the reporter gene is regulated by the binding of the DADD protein encoded by the first polynucleotide to the second protein encoded by the second polynucleotide;

(b) growing the cell in the presence of and in the absence of a compound; and (c) comparing the degree of expression of the reporter gene in the presence of and in the absence of the compound;

wherein the compound is capable of inhibiting DADD death domain binding when a decrease in the degree of expression of the reporter gene occurs. In preferred embodiments, the second protein is a DADD protein or a protein containing the TNF-R death domain. In other preferred embodiments, the cell is a yeast cell and the first polynucleotide is selected from the group consisting of:

(a) a polynucleotide comprising the nucleotide sequence of SEQ ID NO:12;

(b) a polynucleotide comprising the nucleotide sequence of SEQ ID NO:12 from nucleotide 794 to nucleotide 3052;

(c) a polynucleotide comprising the nucleotide sequence of SEQ ID NO:12 from nucleotide 1295 to nucleotide 3052;

(d) a polynucleotide comprising the nucleotide sequence of SEQ ID NO:12 from nucleotide 2726 to nucleotide 2929;

(e) a polynucleotide comprising a fragment of the nucleotide sequence of SEQ ID NO:12;

(f) a polynucleotide encoding a DADD protein comprising the amino acid sequence of SEQ ID NO:13;

(g) a polynucleotide encoding a DADD protein comprising the amino acid sequence of SEQ ID NO:13 from amino acid 167 to amino acid 753;

(h) a polynucleotide encoding a DADD protein comprising the amino acid sequence of SEQ ID NO:13 from amino acid 645 to amino acid 712;

(i) a polynucleotide encoding a DADD protein comprising a fragment of the amino acid sequence of SEQ ID NO:13; and (j) a polynucleotide capable of hybridizing under stringent conditions to any one of the polynucleotides specified in (a)–(i).

In other preferred embodiments, the second polynucleotides is also selected from the preceding list.

DETAILED DESCRIPTION OF THE INVENTION

The EST database (GenBank) was screened using the following sequence from the death domain sequence of human RIP (tblastn):

IRENLGKHWKNCARKLGFTQSQIDEIDH-DYERDGLKEKVYQMLQKWVMREGIKGAT VGKLAQALHQCSRIDLLSSLT (SEQ ID NO:1)

A *homo sapiens* cDNA clone (Length=433) (gb N55392) was identified in the screen. The clone had 39% identity ($15/38$) and 50% homology ($19/38$) with RIP as shown below:

```
RIP     RDGLKEKVYQMLQKWVMREGIKGATVGKLAQALHQCSR   (32-69 SEQ ID NO:1)
        RD L E++ ML  W  R+  +   G L QAL Q  R
clone   RDDLDEQIRHMLFSWAERQAGQPGAVGLLVQALEQSDR   (668-705 SEQ ID NO:13)
```

The sequence of the clone N55392 follows:

TGGACTGGCC AGCCGTGGCC AAAACCTGGG GGTGTCCTAC CGGGAGTGCA (SEQ ID NO:2)

GCGATCCGGC ACGAGTTCCG GGATGATCTG GATGAGCAGA TCCGTCACAT

GCTCTTCTCC TGGGCTGAGC GCCAGGCTGG GCAGCCAGGG NTGTNGGGGC

TCCTGGTGCA GGCCCTGGAG CAGAGTGACC GGCAGACCGT GGCTGAAGAG

GTGCGCGCAG TCTTGGAGCT CGGCCGCCGC AAGTACCAGG ACAGCATCCG

ACGCATGGGC TTGGCCCCAA GGACCCCGCT CTGCCTGGCT CCTCGGGCTC

CACAGCCCCC AGGAGCCTGC CCCAGGCCTT AGGGCCCCAA CAGAACTTTT

TAGGCTGGGC CCAGAATATT CCCCAGGTGG AATGGGCAGA ACCCCAACCN

TTCAAAGTCT CTCCAAGTGTG TGGGGACG NTT

This clone also showed 93% identity with another *Homo sapiens* cDNA clone (gb N39432) over a 159 bp overlap. This clone is 423 bp. The sequence of clone N39432 (3'-->5') follows:

GAAAGAAACA GTGCAGTTTT GTTGCTCACA GGGACCCGTC CCCACACACT (SEQ ID NO:3)

GGAGAGACTT GAAGGTGGGG GCTCTGCATN CCACTGGGGA ATATCTGGGC

CAGCCTAAAA GTCTGTGGGG CCTAGGCTGG GCAGGCTCTG GGGGCTGTGG

AGCCGAGGAG CCAGGCAGAG CGGGGTCCTT GGGGGCCAAG CCATGCGTCG

GATGCTGTCC TGGTACTTGC GGCGGCCGAG CTCCAAGACT GCGCGCACCT

CTTCAGCCAC GTCCTGCCGG TCACTCTGCT CCAGGGCCTG CACCAGGAAG

CCCCACAGCC CCTGGCTGCC CAGCCTNGGC GCTCAGCCAG GAGAAGAGCA

TGTGACGGAT CTGCTCATCC AGATCATCCC GGAACTCGTG CCGGATGCGC

TGCACCTCCC GGTAGACACC CCN

Two sets of PCR primers were designed to amplify 423 bp and 187 bp from human cDNA. An HL60 cDNA library was used as template. The first set was designed to cover the entire sequence of the clone N55392 to amplify 423 bp.
5'primer: GGG GGT GTC CTA CCGGGA GTG CA (23 mer) (SEQ ID NO:4)
3' primer: GAA AGA AAC AGT GCA GTT TTG TTG CTC (27 mer) (SEQ ID NO:5).
The second set was design to amplify 187 bp, using the sequence of both clones identified in the search.
5' primer: CCG CCG CCA GTA CCA GGA CAG CAT (24 mer) (SEQ ID NO:6)
3 primer: CCC ACA CAC TGG AGA GAC TTG AAG (24 mer) (SEQ ID NO:7)
The second set of primers generated a 187 bp fragment with an HL60 library as template. This DNA fragment was used as a probe to screen an HL60 library. The HL60 cDNA library used for this first screening was cloned into the pMT vector for screening in bacteria (colony lifting method).
Two clones (clone1 (SEQ ID NO:8) & clone2 (SEQ ID NO:9)) were isolated from this screen. The sequences are 2844 bp and 2195 bp respectively. Clone 2 contains two potential open reading frames of 642 and 655 amino acids depending of which ATG is considered. The region containing these two ATGs is not present in clone 1. The predicted proteins encoded by clone 2 contain a potential death domain at the C-terminus.

A second library was screened using a random primed U937 cDNA library in lambda phage. The probe used for this screening was a 779 bp fragment from clone 2 from the first screen. This fragment was at the 3'end of clone 2 and was generated by AccI-EcoRI digestion.
Three positive clones were isolated. The sequence of clone32 thus isolated is reported as SEQ ID NO:10. The sequence of these clones gave more information on the 5' end but didn't give the full length cDNA.
To clone the 5'end of the cDNA RACE PCR and primer extended methods were used. In both cases, a primer at the 5'end of clone 32 was used to extend the cDNA toward the 5'end. A human heart and human brain libraries were used for the RACE PCR and a human brain library was used for the primer extended library. Multiple clones were obtained by both techniques. The sequence of clone PE6 thus isolated is reported as SEQ ID NO:11.
Compilation of the sequences for clone 2, clone 32 and clone PE6 give a complete cDNA of 3205 bp for DADD (SEQ ID NO:12). The predicted amino acid sequence encoded thereby is reported as SEQ ID NO:13. There are two potential predicted open reading frames in the same frame, encoding 753 amino acids (for the most upstream ATG at amino acid 1 of SEQ ID NO:13) and 586 amino acids starting at the downstream ATG (amino acid 167 of SEQ ID NO:13). The predicted proteins have a death domain at the C-terminus of the protein (amino acids 645–712 of SEQ ID NO:13).

Rabbit antibodies were raised against the death domain portion of DADD. The antigen was in the form of a GST-DD fusion protein or a MBP-DD fusion protein. Western blot analysis showed a specific band around 55 kDa in Cos cells with the serum 7008 as well as with 7006 to a lesser extent. Multiple human tissue analysis clearly showed a band around the same size (55 kDa) in kidney and liver and to a lesser extent in heart. There was no detection of this protein in brain, lung and skeletal muscle.

Two expression vectors with the two potential open reading frames of 753 and 586 amino acids were expressed with a Flag tag at the N-terminus in Cos cells. Western blot using the serum raised against the DADD death domain showed, in both cases, a band around 55 kDa (as the endogenous protein) plus a band at the expected size of the full length protein around 83 kDa and 65 kDa respectively. On the other hand, a Western blot with the Flag antibody shows a band at the full length size in both cases plus a band at around 30 kDa and 15 kDa respectively.

These results show that the two proteins of 753 aa and 586 aa are cleaved at the same site giving a 55 kDa C-terminal product which comigrate with the endogenous protein originally detected, and an N-terminal product around 30 kDa and 15 kDa respectively.

Co-immunoprecipitation experiments using the serum 7008 raised against the DD of DADD shows that the 30 kDa N-terminus portion of the 753 aa protein is co-immunoprecipitated with the C-terminal part containing the DD. Preliminary experiments also show that DADD co-immunoprecipitate FADD and MADD (Chinnaiyan et al., Cell 81:505–512 (1995); Schierella et al., J. Biol. Chem. 272: 12063–12075 (1997)).

The DADD protein sequence contains five full and two half leucine rich repeats. There are five tandems of 23 amino acid residues plus two half repeats of 12 and 9 residues. This leucine rich region is believed to be a protein—protein interaction domain. The region between this Leu-rich domain and the death domain shows some homology with ankyrin proteins. The homology between DADD and ankyrins correspond to the spectrin domain of the ankyrins, which is know to be a protein—protein interaction domain.

DADD was analysed in assays to investigate different pathways which are known to be activated by TNF (apoptosis, Jnk activation and NFkB activation). DADD activated apoptosis in the SEAP assay (secreted alkaline phosphatase).

The DADD cDNA was deposited with the American Type Culture Collection (10801 University Boulevard, Manassas, Va. 20110-2209) on Apr. 1, 1998, as accession number ATCC 209731. The deposited cDNA encodes the protein of SEQ ID NO: 13 with an additional Flag tag as described above.

Polynucleotides hybridizing to the polynucleotides of the present invention under stringent conditions and highly stringent conditions are also part of the present invention. As used herein, "highly stringent conditions" include, for example, 0.2×SSC at 65° C.; and "stringent conditions" include, for example, 4×SSC at 65° C. or 50% formamide and 4×SSC at 42° C.

For the purposes of the present application, "DADD protein" includes proteins which exhibit DADD protein activity. For the purposes of the present application, a protein is defined as having "DADD protein activity" when it binds to a protein having a death domain, including without limitation the TNF-R death domain or the DADD death domain. Activity can be measured by using any assay which will detect binding to a death domain protein. Examples of such assays include without limitation the interaction trap assays and assays in which TNF-R death domain protein which is affixed to a surface in a manner conducive to observing binding.

Fragments of the DADD protein which are capable of interacting with death domains or which are capable of inhibiting death domain binding (i.e., exhibit DADD protein activity) are also encompassed by the present invention. Fragments of the DADD protein may be in linear form or they may be cyclized using known methods, for example, as described in H. U. Saragovi, et al., Bio/Technology 10, 773–778 (1992) and in R. S. McDowell, et al., J. Amer. Chem. Soc. 114, 9245–9253 (1992), both of which are incorporated herein by reference. Such fragments may be fused to carrier molecules such as immunoglobulins for many purposes, including increasing the valency of DADD protein binding sites. For example, fragments of the DADD protein may be fused through "linker" sequences to the Fc portion of an immunoglobulin. For a bivalent form of the DADD protein, such a fusion could be to the Fc portion of an IgG molecule. Other immunoglobulin isotypes may also be used to generate such fusions. For example, a DADD protein-IgM fusion would generate a decavalent form of the DADD protein of the invention.

The isolated polynucleotide of the invention may be operably linked to an expression control sequence such as the pMT2 or pED expression vectors disclosed in Kaufman et al., Nucleic Acids Res. 19, 4485–4490 (1991), in order to produce the DADD protein recombinantly. Many suitable expression control sequences are known in the art. General methods of expressing recombinant proteins are also known and are exemplified in R. Kaufman, Methods in Enzymology 185, 537–566 (1990). As defined herein "operably linked" means that the isolated polynucleotide of the invention and the expression control sequence are situated within a vector or cell in such a way that the DADD protein is expressed by a host cell which has been transformed (transfected) with the ligated polynucleotide/expression control sequence.

A number of types of cells may act as suitable host cells for expression of the DADD protein. Host cells include, for example, monkey COS cells, Chinese Hamster Ovary (CHO) cells, human kidney 293 cells, human epidermal A431 cells, human Colo205 cells, 3T3 cells, CV-1 cells, other transformed primate cell lines, normal diploid cells, cell strains derived from in vitro culture of primary tissue, primary explants, HeLa cells, mouse L cells, BHK, HL-60, U937, HaK or Jurkat cells.

The DADD protein may also be produced by operably linking the isolated polynucleotide of the invention to suitable control sequences in one or more insect expression vectors, and employing an insect expression system. Materials and methods for baculovirus/insect cell expression systems are commercially available in kit form from, e.g., Invitrogen, San Diego, Calif., U.S.A. (the MaxBac® kit), and such methods are well known in the art, as described in Summers and Smith, *Texas Agricultural Experiment Station Bulletin No.* 1555 (1987), incorporated herein by reference.

Alternatively, it may be possible to produce the DADD protein in lower eukaryotes such as yeast or in prokaryotes such as bacteria Potentially suitable yeast strains include *Saccharomyces cerevisiae, Schizosaccharomyces pombe, Kluyveromyces* strains, *Candida*, or any yeast strain capable of expressing heterologous proteins. Potentially suitable bacterial strains include *Escherichia coli, Bacillus subtilis, Salmonella typhimurium*, or any bacterial strain capable of expressing heterologous proteins. If the DADD protein is made in yeast or bacteria, it may be necessary to modify the protein produced therein, for example by phosphorylation or glycosylation of the appropriate sites, in order to obtain the functional DADD protein. Such covalent attachments may be accomplished using known chemical or enzymatic methods.

The DADD protein of the invention may also be expressed as a product of transgenic animals, e.g., as a component of the milk of transgenic cows, goats, pigs, or sheep which are characterized by somatic or germ cells containing a nucleotide sequence encoding the DADD protein.

The DADD protein of the invention may be prepared by culturing transformed host cells under culture conditions suitable to express the recombinant protein. The resulting expressed protein may then be purified from such culture (i.e., from culture medium or cell extracts) using known purification processes, such as gel filtration and ion exchange chromatography. The purification of the DADD protein may also include an affinity column containing the TNF-R death domain, the DADD death domain or other death domain protein; one or more column steps over such affinity resins as concanavalin A-agarose, heparin-toyopearl® or Cibacrom blue 3GA Sepharose®; one or more steps involving hydrophobic interaction chromatography using such resins as phenyl ether, butyl ether, or propyl ether; or immunoaffinity chromatography.

Alternatively, the DADD protein of the invention may also be expressed in a form which will facilitate purification. For example, it may be expressed as a fusion protein, such as those of maltose binding protein (MBP) or glutathione-S-transferase (GST). Kits for expression and purification of such fusion proteins are commercially available from New England BioLab (Beverly, Mass.) and Pharmacia (Piscataway, N.J.), respectively. The TNF-R ligand protein can also be tagged with an epitope and subsequently purified by using a specific antibody directed to such epitope. One such epitope ("Flag") is commercially available from Kodak (New Haven, Conn.).

Finally, one or more reverse-phase high performance liquid chromatography (RP-HPLC) steps employing hydrophobic RP-HPLC media, e.g., silica gel having pendant methyl or other aliphatic groups, can be employed to further purify the DADD protein. Some or all of the foregoing purification steps, in various combinations, can also be employed to provide a substantially homogeneous isolated recombinant protein. The DADD protein thus purified is substantially free of other mammalian proteins and is defined in accordance with the present invention as an "isolated DADD protein."

DADD proteins may also be produced by known conventional chemical synthesis. Methods for constructing the proteins of the present invention by synthetic means are known to those skilled in the art. The synthetically-constructed protein sequences, by virtue of sharing primary, secondary or tertiary structural and/or conformational characteristics with DADD proteins may possess biological properties in common therewith, including DADD protein activity. Thus, they may be employed as biologically active or immunological substitutes for natural, purified DADD proteins in screening of therapeutic compounds and in immunological processes for the development of antibodies.

The DADD proteins provided herein also include proteins characterized by amino acid sequences similar to those of purified DADD proteins but into which modification are naturally provided or deliberately engineered. For example, modifications in the peptide or DNA sequences can be made by those skilled in the art using known techniques. Modifications of interest in the DADD protein sequences may include the replacement, insertion or deletion of a selected amino acid residue in the coding sequence. For example, one or more of the cysteine residues may be deleted or replaced with another amino acid to alter the conformation of the molecule. Mutagenic techniques for such replacement, insertion or deletion are well known to those skilled in the art (see, e.g., U.S. Pat. No. 4,518,584).

Other fragments and derivatives of the sequences of DADD proteins which would be expected to retain DADD protein activity in whole or in part and may thus be useful for screening or other immunological methodologies may also be easily made by those skilled in the art given the disclosures herein. Such modifications are believed to be encompassed by the present invention.

DADD protein of the invention may also be used to screen for agents which are capable of inhibiting or blocking binding of a DADD protein to the death domain of TNF-R, DADD or other protein, and thus may act as inhibitors of death domain binding and/or the biological activity normally brought on by such binding (e.g., apoptosis). Binding assays using a desired binding protein, immobilized or not, are well known in the art and may be used for this purpose using the DADD protein of the invention. Appropriate screening assays may be cell-based or cell-free. Alternatively, purified protein based screening assays may be used to identify such agents. For example, DADD protein may be immobilized in purified form on a carrier and binding to purified death domain proteins may be measured in the presence and in the absence of potential inhibiting agents. A suitable binding assay may alternatively employ purified death domain protein immobilized on a carrier, with a soluble form of a DADD protein of the invention. Any DADD protein may be used in the screening assays described above.

In such a screening assay, a first binding mixture is formed by combining a death domain-containing protein and DADD protein, and the amount of binding in the first binding mixture ($B_o$) is measured. A second binding mixture is also formed by combining the death domain-containing protein, DADD protein, and the compound or agent to be screened, and the amount of binding in the second binding mixture (B) is measured. The amounts of binding in the first and second binding mixtures are compared, for example, by performing a $B/B_o$ calculation. A compound or agent is considered to be capable of inhibiting binding if a decrease in binding in the second binding mixture as compared to the first binding mixture is observed. The formulation and optimization of binding mixtures is within the level of skill in the art. Such binding mixtures may also contain buffers and salts necessary to enhance or to optimize binding, and additional control assays may be included in the screening assay of the invention.

Alternatively, appropriate screening assays may be cell based. For example, the binding or interaction between a DADD protein and death domain protein can be measured in yeast.

Compounds found to reduce, preferably by at least about 10%, more preferably greater than about 50% or more, the binding activity of DADD protein to a death domain may thus be identified and then secondarily screened in other binding assays, including in vivo assays. By these means compounds having inhibitory activity for DADD death domain binding which may be suitable as anti-inflammatory agents may be identified.

Isolated DADD protein may be useful in treating, preventing or ameliorating inflammatory conditions and other conditions, such as cachexia, autoimmune disease, graft versus host reaction, osteoporosis, colitis, myelogenous leukemia, diabetes, wasting, and atherosclerosis. Isolated DADD protein may be used itself as an inhibitor of TNF-R death domain binding or to design inhibitors of TNF-R death domain binding. Inhibitors of binding of DADD protein to the TNF-R death domain ("TNF-R intracellular binding inhibitors") are also useful for treating such conditions.

The present invention encompasses both pharmaceutical compositions and therapeutic methods of treatment or use which employ isolated DADD protein and/or binding inhibitors of TNF-R intracellular binding.

Isolated DADD protein or binding inhibitors (from whatever source derived, including without limitation from recombinant and non-recombinant cell lines) may be used in a pharmaceutical composition when combined with a pharmaceutically acceptable carrier. Such a composition may also contain (in addition to DADD protein or binding inhibitor and a carrier) diluents, fillers, salts, buffers, stabilizers, solubilizers, and other materials well known in the art. The term "pharmaceutically acceptable" means a non-toxic material that does not interfere with the effectiveness of the biological activity of the active ingredient(s). The characteristics of the carrier will depend on the route of administration. The pharmaceutical composition of the invention may also contain cytokines, lymphokines, or other hematopoietic factors such as M-CSF, GM-CSF, TNF, IL-2, IL-3, IL-4, IL-5, IL-6, IL-7, IL-8, EL-9, G-CSF, Meg-CSF, stem cell factor, and erythropoietin. The pharmaceutical composition may further contain other anti-inflammatory agents. Such additional factors and/or agents may be included in the pharmaceutical composition to produce a synergistic effect with isolated DADD protein or binding inhibitor, or to minimize side effects caused by the isolated DADD protein or binding inhibitor. Conversely, isolated DADD protein or binding inhibitor may be included in formulations of the particular cytokine, lymphokine, other hematopoietic factor, thrombolytic or anti-thrombotic factor, or anti-inflammatory agent to minimize side effects of the cytokine, lymphokine, other hematopoietic factor, thrombolytic or anti-thrombotic factor, or anti-inflammatory agent.

The pharmaceutical composition of the invention may be in the form of a liposome in which isolated DADD protein or binding inhibitor is combined, in addition to other pharmaceutically acceptable carriers, with amphipathic agents such as lipids which exist in aggregated form as micelles, insoluble monolayers, liquid crystals, or lamellar layers in aqueous solution. Suitable lipids for liposomal formulation include, without limitation, monoglycerides, diglycerides, sulfatides, lysolecithin, phospholipids, saponin, bile acids, and the like. Preparation of such liposomal formulations is within the level of skill in the art, as disclosed, for example, in U.S. Pat. No. 4,235,871; U.S. Pat. No. 4,501,728; U.S. Pat. No. 4,837,028; and U.S. Pat. No. 4,737,323, all of which are incorporated herein by reference.

As used herein, the term "therapeutically effective amount" means the total amount of each active component of the pharmaceutical composition or method that is sufficient to show a meaningful patient benefit, i.e., treatment, healing, prevention or amelioration of an inflammatory response or condition, or an increase in rate of treatment, healing, prevention or amelioration of such conditions. When applied to an individual active ingredient, administered alone, the term refers to that ingredient alone. When applied to a combination, the term refers to combined amounts of the active ingredients that result in the therapeutic effect, whether administered in combination, serially or simultaneously.

In practicing the method of treatment or use of the present invention, a therapeutically effective amount of isolated DADD protein or binding inhibitor is administered to a mammal having a condition to be treated. Isolated DADD protein or binding inhibitor may be administered in accordance with the method of the invention either alone or in combination with other therapies such as treatments employing cytokines, lymphokines or other hematopoietic factors. When co-administered with one or more cytokines, lymphokines or other hematopoietic factors, isolated DADD protein or binding inhibitor may be administered either simultaneously with the cytokine(s), lymphokine(s), other hematopoietic factor(s), thrombolytic or anti-thrombotic factors, or sequentially. If administered sequentially, the attending physician will decide on the appropriate sequence of administering isolated DADD protein or binding inhibitor in combination with cytokine(s), lymphokine(s), other hematopoietic factor(s), thrombolytic or anti-thrombotic factors.

Administration of isolated DADD protein or binding inhibitor used in the pharmaceutical composition or to practice the method of the present invention can be carried out in a variety of conventional ways, such as oral ingestion, inhalation, or cutaneous, subcutaneous, or intravenous injection. Intravenous administration to the patient is preferred.

When a therapeutically effective amount of isolated DADD protein or binding inhibitor is administered orally, isolated DADD protein or binding inhibitor will be in the form of a tablet, capsule, powder, solution or elixir. When administered in tablet form, the pharmaceutical composition of the invention may additionally contain a solid carrier such as a gelatin or an adjuvant. The tablet, capsule, and powder contain from about 5 to 95% isolated DADD protein or binding inhibitor, and preferably from about 25 to 90% isolated DADD protein or binding inhibitor. When administered in liquid form, a liquid carrier such as water, petroleum, oils of animal or plant origin such as peanut oil, mineral oil, soybean oil, or sesame oil, or synthetic oils may be added. The liquid form of the pharmaceutical composition may further contain physiological saline solution, dextrose or other saccharide solution, or glycols such as ethylene glycol, propylene glycol or polyethylene glycol. When administered in liquid form, the pharmaceutical composition contains from about 0.5 to 90% by weight of isolated DADD protein or binding inhibitor, and preferably from about 1 to 50% isolated DADD protein or binding inhibitor.

When a therapeutically effective amount of isolated DADD protein or binding inhibitor is administered by intravenous, cutaneous or subcutaneous injection, isolated DADD protein or binding inhibitor will be in the form of a pyrogen-free, parenterally acceptable aqueous solution. The preparation of such parenterally acceptable protein solutions, having due regard to pH, isotonicity, stability, and the like, is within the skill in the art. A preferred pharmaceutical composition for intravenous, cutaneous, or subcutaneous injection should contain, in addition to isolated DADD protein or binding inhibitor, an isotonic vehicle such as Sodium Chloride Injection, Ringer's Injection, Dextrose Injection, Dextrose and Sodium Chloride Injection, Lactated Ringer's Injection, or other vehicle as known in the art. The pharmaceutical composition of the present invention may also contain stabilizers, preservatives, buffers, antioxidants, or other additives known to those of skill in the art.

The amount of isolated DADD protein or binding inhibitor in the pharmaceutical composition of the present invention will depend upon the nature and severity of the condition being treated, and on the nature of prior treatments which the patient has undergone. Ultimately, the attending physician will decide the amount of isolated DADD protein or binding inhibitor with which to treat each individual patient. Initially, the attending physician will administer low doses of isolated DADD protein or binding inhibitor and observe the patient's response. Larger doses of isolated DADD protein or binding inhibitor may be administered until the optimal therapeutic effect is obtained for the patient, and at that point the dosage is not increased further. It is contemplated that the various pharmaceutical compositions used to practice the method of the present invention should contain about 0.1 μg to about 100 mg of isolated DADD protein or binding inhibitor per kg body weight.

The duration of intravenous therapy using the pharmaceutical composition of the present invention will vary, depending on the severity of the disease being treated and the condition and potential idiosyncratic response of each individual patient. It is contemplated that the duration of each application of the isolated DADD protein or binding inhibitor will be in the range of 12 to 24 hours of continuous intravenous administration. Ultimately the attending physician will decide on the appropriate duration of intravenous therapy using the pharmaceutical composition of the present invention.

Isolated DADD protein of the invention may also be used to immunize animals to obtain polyclonal and monoclonal antibodies which specifically react with the DADD protein and which may inhibit TNF-R death domain binding. Such antibodies may be obtained using either the entire DADD protein or fragments of DADD protein as an immunogen. The peptide immunogens additionally may contain a cysteine residue at the carboxyl terminus, and are conjugated to a hapten such as keyhole limpet hemocyanin (KLH). Methods for synthesizing such peptides are known in the art, for example, as in R. P. Merrifield, J. Amer. Chem. Soc. 85, 2149–2154 (1963); J. L. Krstenansky, et al., FEBS Lett. 211, 10 (1987).

Monoclonal antibodies binding to DADD protein or to complex carbohydrate moieties characteristic of the DADD glycoprotein may be useful diagnostic agents for the immunodetection of TNF-R ligand protein.

Neutralizing monoclonal antibodies binding to DADD protein or to complex carbohydrates characteristic of DADD glycoprotein may also be useful therapeutics for both inflammatory conditions and also in the treatment of some forms of cancer where abnormal expression of DADD protein is involved. These neutralizing monoclonal antibodies are capable of blocking the signaling function of the DADD protein. By blocking the binding of DADD protein, certain biological responses to TNF are either abolished or markedly reduced. In the case of cancerous cells or leukemic cells, neutralizing monoclonal antibodies against DADD protein may be useful in detecting and preventing the metastatic spread of the cancerous cells, which may be mediated by the DADD protein. The present invention also provides genes corresponding to the polynucleotide sequences disclosed herein. "Corresponding genes" are the regions of the genome that are transcribed to produce the mRNAs from which cDNA polynucleotide sequences are derived and may include contiguous regions of the genome necessary for the regulated expression of such genes. Corresponding genes may therefore include but are not limited to coding sequences, 5' and 3' untranslated regions, alternatively spliced exons, introns, promoters, enhancers, and silencer or suppressor elements. The corresponding genes can be isolated in accordance with known methods using the sequence information disclosed herein. Such methods include the preparation of probes or primers from the disclosed sequence information for identification and/or amplification of genes in appropriate genomic libraries or other sources of genomic materials. An "isolated gene" is a gene that has been separated from the adjacent coding sequences, if any, present in the genome of the organism from which the gene was isolated.

Organisms that have enhanced, reduced, or modified expression of the gene(s) corresponding to the polynucleotide sequences disclosed herein are provided. The desired change in gene expression can be achieved through the use of antisense polynucleotides or ribozymes that bind and/or cleave the mRNA transcribed from the gene (Albert and Morris, 1994, Trends Pharmacol. Sci. 15(7): 250–254; Lavarosky et al., 1997, Biochem. Mol. Med. 62(1): 11–22; and Hampel, 1998, Prog. Nucleic Acid Res. Mol. Biol. 58: 1–39; all of which are incorporated by reference herein). Transgenic animals that have multiple copies of the gene(s) corresponding to the polynucleotide sequences disclosed herein, preferably produced by transformation of cells with genetic constructs that are stably maintained within the transformed cells and their progeny, are provided. Transgenic animals that have modified genetic control regions that increase or reduce gene expression levels, or that change temporal or spatial patterns of gene expression, are also provided (see European Patent No. 0 649 464 B1, incorporated by reference herein). In addition, organisms are provided in which the gene(s) corresponding to the polynucleotide sequences disclosed herein have been partially or completely inactivated, through insertion of extraneous sequences into the corresponding gene(s) or through deletion of all or part of the corresponding gene(s). Partial or complete gene inactivation can be accomplished through insertion, preferably followed by imprecise excision, of transposable elements (Plasterk, 1992, Bioessays 14(9): 629–33; Zwaal et al., 1993, Proc. Natl. Acad. Sci. USA 90(16): 7431–7435; Clark et al., 1994, Proc. Natl. Acad. Sci. USA 91(2): 719–722; all of which are incorporated by reference herein), or through homologous recombination, preferably detected by positive/negative genetic selection strategies (Mansour et al., 1988, Nature 336: 348–352; U.S. Pat. Nos. 5,464,764; 5,487,992; 5,627,059; 5,631,153; 5,614, 396; 5,616,491; and 5,679,523; all of which are incorporated by reference herein). These organisms with altered gene expression are preferably eukaryotes and more preferably are mammals. Such organisms are useful for the development of non-human models for the study of disorders involving the corresponding gene(s), and for the development of assay systems for the identification of molecules that interact with the protein product(s) of the corresponding gene(s).

All references cited herein are incorporated as if fully set forht herein.

What is claimed is:

1. An isolated polynucleotide comprising a nucleotide sequence that hybridizes under conditions of incubation at 42° C. in 50% formamide and 4×SSC to a polynucleotide comprising the complement of the nucleotide sequence of SEQ ID NO:12, wherein said isolated polynucleotide encodes a protein comprising a death domain and a leucine-rich domain, and wherein said protein activates apoptosis.

2. The isolated polynucleotide of claim 1 wherein said polynucleotide is operably linked to an expression control sequence.

3. An isolated host cell transformed with the isolated polynucleotide of claim 2.

4. The host cell of claim 3, wherein said isolated host cell is a mammalian cell.

5. A process for producing a protein, which comprises;
   (a) growing a culture of the host cell of claim 4 in a suitable culture medium; and
   (b) purifying the protein from the culture.

6. An isolated polynucleotide comprising the nucleotide sequence of SEQ ID NO:12, or a complete complement thereof.

7. An isolated polynucleotide comprising the nucleotide sequence of SEQ ID NO:12 from nucleotide 794 to nucleotide 3052, or a complete complement thereof.

8. An isolated polynucleotide comprising the nucleotide sequence of SEQ ID NO:12 from nucleotide 1295 to nucleotide 3052, or a complete complement thereof.

9. An isolated polynucleotide encoding a polypeptide comprising the amino acid sequence of SEQ ID NO:13, or a complete complement thereof.

10. An isolated polynucleotide encoding a polypeptide comprising the amino acid sequence of SEQ ID NO:13 from amino acid 167 to amino acid 753, or a complete complement thereof.

11. An isolated polynucleotide encoding a polypeptide comprising an amino acid sequence encoded by the DNA insert of the plasmid deposited with ATCC as Accession Number 209731, or the complete complement thereof.

12. An isolated polynucleotide that encodes a protein of about 55 kDA to 83 kDa, wherein said protein comprises a death domain comprising amino acid residues 645–712 of SEQ ID NO:13.

13. An isolated polynucleotide that hybridizes under conditions of incubation at 42° C. in 50% formamide and 4×SSC to the complement of a polynucleotide comprising the nucleotide sequence of SEQ ID NO:12, wherein said isolated polynucleotide encodes a protein comprising a death domain and a leucine-rich domain, and wherein said protein interacts with a FADD or MADD protein.

14. An isolated polynucleotide comprising a nucleotide sequence of at least 779 nucleotides in length encoding a protein having death activator death domain ("DADD") activity, wherein said complement of said polynucleotide hybridizes under conditions of incubation at 42° C. in 50% formamide and 4×SSC to a polynucleotide comprising the nucleotide sequence of SEQ ID NO:12.

* * * * *

SEQUENCE LISTING (1) GENERAL INFORMATION:

(iii) NUMBER OF SEQUENCES: 13

(2) INFORMATION FOR SEQ ID NO:1:

(i) SEQUENCE CHARACTERISTICS:

```
        (A) LENGTH: 77 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:1:

Ile Arg Glu Asn Leu Gly Lys His Trp Lys Asn Cys Ala Arg Lys Leu
1               5                  10                  15

Gly Phe Thr Gln Ser Gln Ile Asp Glu Ile Asp His Asp Tyr Glu Arg
                20                  25                  30

Asp Gly Leu Lys Glu Lys Val Tyr Gln Met Leu Gln Lys Trp Val Met
            35                  40                  45

Arg Glu Gly Ile Lys Gly Ala Thr Val Gly Lys Leu Ala Gln Ala Leu
    50                  55                  60

His Gln Cys Ser Arg Ile Asp Leu Leu Ser Ser Leu Thr
65                  70                  75

(2) INFORMATION FOR SEQ ID NO:2:

(i) SEQUENCE CHARACTERISTICS:
        (A) LENGTH: 433 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:2:

TGGACTGGCC AGCCGTGGCC AAAACCTGGG GGTGTCCTAC CGGGAGTGCA GCGATCCGGC      60

ACGAGTTCCG GGATGATCTG GATGAGCAGA TCCGTCACAT GCTCTTCTCC TGGGCTGAGC     120

GCCAGGCTGG GCAGCCAGGG NTGTNGGGGC TCCTGGTGCA GGCCCTGGAG CAGAGTGACC     180

GGCAGACCGT GGCTGAAGAG GTGCGCGCAG TCTTGGAGCT CGGCCGCCGC AAGTACCAGG     240

ACAGCATCCG ACGCATGGGC TTGGCCCCAA GGACCCCGCT CTGCCTGGCT CCTCGGGCTC     300

CACAGCCCCC AGGAGCCTGC CCCAGGCCTT AGGGCCCCAA CAGAACTTTT TAGGCTGGGC     360

CCAGAATATT CCCCAGGTGG AATGGGCAGA ACCCCAACCN TTCAAAGTCT CTCCAAGTGT     420

GTGGGGACG NTT                                                        433

(2) INFORMATION FOR SEQ ID NO:3:

(i) SEQUENCE CHARACTERISTICS:
        (A) LENGTH: 423 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:3:

GAAAGAAACA GTGCAGTTTT GTTGCTCACA GGGACCCGTC CCCACACACT GGAGAGACTT      60

GAAGGTGGGG GCTCTGCATN CCACTGGGGA ATATCTGGGC CAGCCTAAAA GTCTGTGGGG     120

CCTAGGCTGG GCAGGCTCTG GGGGCTGTGG AGCCGAGGAG CCAGGCAGAG CGGGGTCCTT     180

GGGGGCCAAG CCATGCGTCG GATGCTGTCC TGGTACTTGC GGCGGCCGAG CTCCAAGACT     240

GCGCGCACCT CTTCAGCCAC GTCCTGCCGG TCACTCTGCT CCAGGGCCTG CACCAGGAAG     300

CCCCACAGCC CCTGGCTGCC CAGCCTNGGC GCTCAGCCAG GAGAAGAGCA TGTGACGGAT     360

CTGCTCATCC AGATCATCCC GGAACTCGTG CCGGATGCGC TGCACCTCCC GGTAGACACC     420
```

CCN                                                               423

(2) INFORMATION FOR SEQ ID NO:4:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:4:

GGGGGTGTCC TACCGGGAGT GCA                                          23

(2) INFORMATION FOR SEQ ID NO:5:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:5:

GAAAGAAACA GTGCAGTTTT GTTGCTC                                      27

(2) INFORMATION FOR SEQ ID NO:6:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:6:

CCGCCGCCAG TACCAGGACA GCAT                                         24

(2) INFORMATION FOR SEQ ID NO:7:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:7:

CCCACACACT GGAGAGACTT GAAG                                         24

(2) INFORMATION FOR SEQ ID NO:8:

(i) SEQUENCE CHARACTERISTICS:
        (A) LENGTH: 2884 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:8:

-continued

```
GAATTCCGTC GACTCTAGAG GGCTCTGGGG GCCCTCCCCG CCCTCACCTT CCTCATAGTG      60
ACACACAACC GCCTGCAGAC GCTGCCCCCA GCACTGGGGG CCCTATCCAC CCTGCAGCGC     120
CTCGATCTCT CTCAGAATCT GCTGGACACG CTACCTCCTG AGATTGGAGG CCTGGGCAGC     180
CTCCTGGAGC TCAACCTGGC CTCCCAACCG GCTGCAGAGC CTCCCAGCCT CTCTGGGTGA     240
GTAGCCCCTG CGCCCCGACA CACTGGCCCC ACGGGAGGGT CCCTGAAGCC TGCCTGTCTT     300
CTGCAGGGGC CTCTGCACCC ACAGGCTTGG TCCACAGCTG CCTCTTGGTT GTCCCTCCAC     360
CTCCCTGGCC TTTGAGACTC CCTCAGTGGC TTCGTCAGAG TTCTCTGAGC CCAGCTGTGG     420
AGGAGAGTCT GAAACAGCTG CTCTGGGAGG CGGCAGCAGG AGTGTCCCAG CGCCGTGGGC     480
TGGGCTGGTG CCAAGCCTAA GCCAGCACCT GCCCGCAGCG GGACTTCGGT CCTTGCGGCT     540
CCTTGTCCTG CACAGCAACC TCCTGGCCTC TGTGCCAGCT GACTTGGCCC GCCTTCCACT     600
CCTCACCCGG CTCGACCTGA GGGACAACCA GCTCCGGGAC CTGCCCCCTG AGCTGCTAGA     660
CGCCCCCTTT GTGCGCCTGC AGGGGAACCC CCTGGGTGAG GCCTCGCCAG ACGCCCCGAG     720
TTCACCAGTG GCAGCCCTCA TTCCAGAAAT GCCCAGACTG TTCCTGACCT CAGATTTGGA     780
CAGCTTTCCT GTGACCCCTC GAGGCTGCTC AGTGACCCTG GCCTGTGGCG TCCGCCTGCA     840
GTTCCCAGCG GGAGCCACCG CCACCCCCAT CACCATCCGC TATCGGCTGC TGCTGCCGGA     900
GCCAGGCCTC GTCCCCCTGG GTCCTCATGA CGCCCTGCTC AGCCATGTGC TGGAGCTGCA     960
GCCCCATGGG GTGGCCTTCC AGCAGGATGT GGGGCTGTGG CTGCTCTTCA CCCCACCGCA    1020
GGCCCGGCGC TGCCGTGAAG TGGTGGTCAG GACCCGGAAT GACAACAGCT GGGGTGACCT    1080
GGAGACCTAC CTGGAGGAAG AGGCACCCCA GCGGCTCTGG GCTCACTGCC AGGTGCCCCA    1140
CTTCTCCTGG TTCCTTGTGG TTTCCCGCCC TGTGTCCAAT GCCTGCCTGG TGCCACCGGA    1200
GGGGACACTG CTGTGCTCCT CGGGTCATCC TGGGGTCAAA GTCATCTTCC CCCCTGGGGC    1260
CACTGAGGAG CCTCGTCGAG TCTCCATGCA GGTGGTGCGC ATGGCTGGCC GAGAGCTGCA    1320
GGCCCTCCTG GGAGAACCAG AGGCTGCAGT GAGCCCCCTG CTGTGCCTGT CACAGAGCGG    1380
TCCCCCCAGC TTCCTCCAAC CGGTCACCGT GCAGCTGCCT CTGCCCTCTG GCATCACAGG    1440
CCTCAGTCTG GACCGCTCCC GCCTGCACCT GTTGTACTGG GCCCCTCCTG CAGCCACCTG    1500
GGATGACATC ACAGCTCAGG TGGTCCTGGA GCTCACCCAC CTGTACGCAC GCTTCCAGGT    1560
CACACACTTC TCCTGGTCAG TGCCCCCCAG CTTTCTCAGC CCCCCTCCCC CAGTCTGTAC    1620
AGCCCTCCTC ACCCCCAGCT CTCCCAGGTA CTGGCTCTGG TACACCACCA AGAACTGTGT    1680
GGGAGGCCTG GCTCGGAAGG CCTGGGAGCG GCTGCGGCTG CACCGTGTGA ACCTCATCGC    1740
TCTGCAGCGG CGCCGGGACC CTGAGCAGGT CCTGCTGCAG TGCCTGCCCC GAAACAAGGT    1800
GGACGCCACC CTTCGGCGGC TGCTGGAGCG GTACCGGGGC CCCGAGCCCT CTGACACGGT    1860
GGAGATGTTC GAGGGCGAAG AGTTCTTTGC GGCCTTCGAG CGCGGCATCG ACGTGGATGC    1920
TGACCGCCCT GACTGTGTGG AGGGCAGAAT CTGCTTTGTC TTCTACTCGC ACCTGAAGAA    1980
TGTGAAGGAG GTATACGTGA CCACCACTCT GGACCGGGAG GCTCAGGCTG TGCGGGGCCA    2040
GGTGTCCTTC TACCGTGGCG CGGTGCCTGT GCGGGTGCCC GAGGAGGCTG AGGCTGCCCG    2100
GCAGAGGAAG GGCGCAGACG CCCTGTGGAT GGCCACTCTG CCCATCAAGC TGCCGGTGGG    2160
ACTGAGGGAC AGCAGAGGGG CGGGGCAGGA CCGAGGCCCA GGGGTGACCA GGGTGACATG    2220
GTGGAGTTGG GGGTGGAGCC CAGGGCTTAA TGCACTTTTT CCTTCCAACA GAGACTTCGA    2280
GGGTCCGAGG GGCCACGGCG GGGGGCTGGC CTCTCCTTGG CACCCTTGAA TCTGGGAGAT    2340
```

```
GCCGAGACCG GCTTTCTGAC GCAGAGCAAC CTGCTGAGTG TGGCTGGGCG TCTGGGTCTG    2400

GACTGGCCAG CCGTGGCCCT GCACCTGGGG GTGTCCTACC GGGAGGTGCA GCGCATCCGG    2460

CACGAGTTCC GGGATGATCT GGATGAGCAG ATCCGTCACA TGCTCTTCTC CTGGGCTGAG    2520

CGCCAGGCTG GCAGCCAGG GGCTGTGGGG CTCCTGGTGC AGGCCCTGGA GCAGAGTGAC    2580

CGGCAGGACG TGGCTGAAGA GGTGCGCGCA GTCTTGGAGC TCGGCCGCCG CAAGTACCAG    2640

GACAGCATCC GACGCATGGG CTTGGCCCCC AAGGACCCCG CTCTGCCTGG CTCCTCGGCT    2700

CCACAGCCCC CAGAGCCTGC CCAGGCCTAG GCCCCACAGA CTTTTAGGCT GGCCCAGATA    2760

TTCCCCAGTG GATGGGCAGA GCCCCCACCT TCAAGTCTCT CCAGTGTGTG GGGACGGGTC    2820

CCTGTGAGCA ACAAAACTGC ACTGTTTCTT TCAAAAAAAA AAAACTCTAG AGTCGACGGA    2880

ATTC                                                                2884
```

(2) INFORMATION FOR SEQ ID NO:9:

(i) SEQUENCE CHARACTERISTICS:
        (A) LENGTH: 2209 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:9:

```
TCTAGAGGTC CCCCTGGGTC CTCATGACGC CCTGCTCAGC CATGTGCTGG AGCTGCAGCC      60

CCATGGGGTG GCCTTCCAGC AGGCATGGAC AGGGCGTGGC GGGGGCAGTG TGTGGGCCAG     120

GGCATGGCAG GGGCAGTGTG CGGGCCCGGG CGTGGCTCCA GCGCTCACAC CATCCTTGTC     180

TGGCAGGATG TGGGGCTGTG GCTGCTCTTC ACCCCACCGC AGGCCCGGCG CTGCCGTGAA     240

GTGGTGGTCA GGACCCGGAA TGACAACAGC TGGGGTGACC TGGAGACCTA CCTGGAGGAA     300

GAGGCACCCC AGGTGAGGGC CACCCAGGCC TGCCGGTGGC GAGTGGAGAG CTGCTGCCCT     360

GAGCCGTGCA CCTCTGCCCA GAGCCTCACC CTGGCACCTT CCACCCTGCC CCGTCCCTCC     420

TGGATCCTGC TTCCCTATGT CCCTGGCACC TTCCACCCCA CCCCGTCCCT CCTGGATCCT     480

GCTTCCCTGT GTCCCTGGCA CCTTCCACCC CACCCCGTCC CTCCTGGATC CTGCTCCCTG     540

TGTCCCTGGC ACCTNTCCAC CCCGCCCCGT CTCTCCTGGA TNCTGCTCCC TGTGTCCCTG     600

ACTGGCTGTG CCCTGACCCA GGCTCCTGTG ACCTCCTCTC TCCCCCCATC CCAGCGGCTC     660

TGGGCTCACT GCCAGGTGCC CCACTTCTCC TGGTTCCTTG TGGTTTCCCG CCCTGTGTCC     720

AATGCCTGCC TGGTGCCACC GGAGGGGACA CTGCTGTGCT CCTCGGGTCA TCCTGGGGTC     780

AAAGTCATCT TCCCCCCTGG GGCCACTGAG GAGCCTCGTC GAGTCTCCAT GCAGGTGGTG     840

CGCATGGCTG GCCGAGAGCT GCAGGCCCTC CTGGGAGAAC CAGAGGCTGC AGTGAGCCCC     900

CTGCTGTGCC TGTCACAGAG CGGTCCCCCC AGCTTCCTCC AACCGGTCAC CGTGCAGCTG     960

CCTCTGCCCT CTGGCATCAC AGGCCTCAGT CTGGACCGCT CCCGCCTGCA CCTGTTGTAC    1020

TGGGCCCCTC CTGCAGCCAC CTGGGATGAC ATCACAGCTC AGGTGGTCCT GGAGCTCACC    1080

CACCTGTACT GGCTCTGGTA CACCACCAAG AACTGTGTGG GAGGCCTGGC TCGGAAGGCC    1140

TGGGAGCGGC TGCGGCTGCA CCGTGTGAAC CTCATCGCTC TGCAGCGGCG CCGGGACCCT    1200

GAGCAGGTCC TGCTGCAGTG CCTGCCCCGA AACAAGGTGG ACGCCACCCT TCGGCGGCTG    1260

CTGGAGCGGT ACCGGGGCCC CGAGCCCTCT GACACGGTGG AGATGTTCGA GGGCGAAGAG    1320

TTCTTTGCGG CCTTCGAGCG CGGCATCGAC GTGGATGCTG ACCGCCCTGA CTGTGTGGAG    1380
```

| | |
|---|---|
| GGCAGAATCT GCTTTGTCTT CTACTCGCAC CTGAAGAATG TGAAGGAGGT ATACGTGACC | 1440 |
| ACCACTCTGG ACCGGGAGGC TCAGGCTGTG CGGGGCCAGG TGTCCTTCTA CCGTGGCGCG | 1500 |
| GTGCCTGTGC GGGTGCCCGA GGAGGCTGAG GCTGCCCGGC AGAGGAAGGG CGCAGACGCC | 1560 |
| CTGTGGATGG CCACTCTGCC CATCAAGCTG CCGAGACTTC GAGGGTCCGA GGGGCCACGG | 1620 |
| CGGGGGGCTG GCCTCTCCTT GGCACCCTTG AATCTGGGAG ATGCCGAGAC CGGCTTTCTG | 1680 |
| ACGCAGAGCA ACCTGCTGAG TGTGGCTGGG CGTCTGGGTC TGGACTGGCC AGCCGTGGCC | 1740 |
| CTGCACCTGG GGGTGTCCTA CCGGGAGGTG CAGCGCATCC GGCACGAGTT CCGGGATGAT | 1800 |
| CTGGATGAGC AGATCCGTCA CATGCTCTTC TCCTGGGCTG AGCGCCAGGC TGGGCAGCCA | 1860 |
| GGGGCTGTGG GGCTCCTGGT GCAGGCCCTG GAGCAGAGTG ACCGGCAGGA CGTGGCTGAA | 1920 |
| GAGGTGCGCG CAGTCTTGGA GCTCGGCCGC CGCAAGTACC AGGACAGCAT CCGACGNATG | 1980 |
| GGCTTGGCCC CCAAGGACCC CGTTCTGCCT GGCTCCTCGG CTCCACAGCC CCAGAGCCT | 2040 |
| GCCCAGGCAT AGGCCCCACA GAATTTTAGG CTGGCCCAGA TATTCCCCAG TGGATGGGCA | 2100 |
| GAGCCCCCAC CTTCAAGTCT CTCCAGTGTG TGGGACGGG TCCCTGTGAG CAACAAAACT | 2160 |
| GCACTGTTTC TTTCACCTCG AAAAAAAAAA AAAAAAAAA AACTCTAGA | 2209 |

(2) INFORMATION FOR SEQ ID NO:10:

(i) SEQUENCE CHARACTERISTICS:
        (A) LENGTH: 1903 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:10:

| | |
|---|---|
| GGCCTGGGCA GCCTCCTGGA GCTCAACCTG GCCTCCAACC GGCTGCAGAG CCTCCCAGCC | 60 |
| TCTCTGGCGG GACTTCGGTC CTTGCGGCTC CTTGTCCTGC ACAGCAACCT CCTGGCCTCT | 120 |
| GTGCCAGCTG ACTTGGCCCG CCTTCCACTC CTCACCCGGC TCGACCTGAG GGACAACCAG | 180 |
| CTCCGGGACC TGCCCCCTGA GCTGCTAGAC GCCCCCTTTG TGCGCCTGCA GGGGAACCCC | 240 |
| CTGGGTGAGG CCTCGCCAGA CGCCCCGAGT TCACCAGTGG CAGCCCTCAT TCCAGAAATG | 300 |
| CCCAGACTGT TCCTGACCTC AGATTTGGAC AGCTTTCCTG TGACCCCTCG AGGCTGCTCA | 360 |
| GTGACCCTGG CCTGTGGCGT CCGCCTGCAG TTCCCAGCGG GAGCCACCGC CACCCCCATC | 420 |
| ACCATCCGCT ATCGGCTGCT GCTGCCGGAG CCAGGCCTCG TCCCCCTGGG TCCTCATGAC | 480 |
| GCCCTGCTCA GCCATGTGCT GGAGCTGCAG CCCCATGGGG TGGCCTTCCA GCAGGATGTG | 540 |
| GGGCTGTGGC TGCTCTTCAC CCCACCGCAG GCCCGGCGCT GCCGTGAAGT GGTGGTCAGG | 600 |
| ACCCGGAATG ACAACAGCTG GGGTGACCTG GAGACCTACC TGGAGGAAGA GGCACCCCAG | 660 |
| CGGCTCTGGG CTCACTGCCA GGTGCCCCAC TTCTCCTGGT TCCTTGTGGT TTCCCGCCCT | 720 |
| GTGTCCAATG CCTGCCTGGT GCCACCGGAG GGGACACTGC TGTGCTCCTC GGGTCATCCT | 780 |
| GGGGTCAAAG TCATCTTCCC CCCTGGGGCC ACTGAGGAGC CTCGTCGAGT CTCCATGCAG | 840 |
| GTGGTGCGCA TGGCTGGCCG AGAGCTGCAG GCCCTCCTGG GAGAACCAGA GGCTGCAGTG | 900 |
| AGCCCCCTGC TGTGCCTGTC ACAGAGCGGT CCCCCCAGCT TCCTCCAACC GGTCACCGTG | 960 |
| CAGCTGCCTC TGCCCTCTGG CATCACAGGC CTCAGTCTGG ACCGCTCCCG CCTGCACCTG | 1020 |
| TTGTACTGGG CCCCTCCTGC AGCCACCTGG GATGACATCA CAGCTCAGGT GGTCCTGGAG | 1080 |
| CTCACCCACC TGTACTGGCT CTGGTACACC ACCAAGAACT GTGTGGGAGG CCTGGCTCGG | 1140 |

| | |
|---|---|
| AAGGCCTGGG AGCGGCTGCG GCTGCACCGT GTGAACCTCA TCGCTCTGCA GCGGCGCCGG | 1200 |
| GACCCTGAGC AGGTCCTGCT GCAGTGCCTG CCCCGAAACA AGGTGGACGC CACCCTTCGG | 1260 |
| CGGCTGCTGG AGCGGTACCG GGGCCCCGAG CCCTCTGACA CGGTGGAGAT GTTCGAGGGC | 1320 |
| GAAGAGTTCT TTGCGGCCTT CGAGCGCGGC ATCGACGTGG ATGCTGACCG CCCTGACTGT | 1380 |
| GTGGAGGGCA GAATCTGCTT TGTCTTCTAC TCGCACCTGA AGAATGTGAA GGAGGTGTCC | 1440 |
| TTCTACCGTG GCGCGGTGCC TGTGCGGGTG CCCGAGGAGG CTGAGGCTGC CCGGCAGAGG | 1500 |
| AAGGGCGCAG ACGCCCTGTG GATGGCCACT CTGCCCATCA AGCTGCCGAG ACTTCGAGGG | 1560 |
| TCCGAGGGGC CACGGCGGGG GGCTGGCCTC TCCTTGGCAC CCTTGAATCT GGGAGATGCC | 1620 |
| GAGACCGGCT TTCTGACGCA GAGCAACCTG CTGAGTGTGG CTGGGCGTCT GGGTCTGGAC | 1680 |
| TGGCCAGCCG TGGCCCTGCA CCTGGGGGTG TCCTACCGGG AGGTGCAGCG CATCCGGCAC | 1740 |
| GAGTTCCGGG ATGATCTGGA TGAGCAGATC CGTCACATGC TCTTCTCCTG GGCTGAGCGC | 1800 |
| CAGGCTGGGA AGCCAGGGGC TGTGGGGCTC CTGGTGCAGG CCCTGGAGCA GAGTGACCGG | 1860 |
| CAGGACGTGG CTGAAGAGGT GCGCGCAGTC TTGGAGCTCG GCC | 1903 |

(2) INFORMATION FOR SEQ ID NO:11:

(i) SEQUENCE CHARACTERISTICS:
        (A) LENGTH: 1030 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:11:

| | |
|---|---|
| GTCGACTCTC CTGCGTAGCC ATGGCGGTCC CATTCCCCAA CCCTCTTTCC AGTGGTGACC | 60 |
| CAAGCCTCCG GGGTTCAGGG TGACCACNAT GTCTCCCCCA CTCTGCATCC CAGGCCCATA | 120 |
| TGGCCTGGCT CTANAGCTCC CCACTCCATC CANAGTCCCT GTTTCCCCAA AGAGAANGGC | 180 |
| CCACCCCGGC TCCCGCTCAC TCCTCCTCCT GCCTCTGCAT CTTCCCCGGG CGCTGCCTGG | 240 |
| ACAGGCCTGC CTGCGTGCTG GGACATGTCT GGCCTCCAAG GACCGTCGGT GGGCGATGGC | 300 |
| TGCAACGGTG GAGGGGCCAG AGCTGGAGGC AGCTGCTGCC GCAGGAGATG CTTCAGAGGA | 360 |
| TTCGGACGCA GGGTCCAGGG CGCTTCCTTT CCTGGGCGGC AACCGGCTGA GCTTGGACCT | 420 |
| GTACCCCGGG GGCTGCCAGC AGCTGCTGCA CCTGTGTGTC CAGCAGCCTC TTCAGCTGCT | 480 |
| GCAGGTGGAA TTCTTGCGTC TGAGCACTCA CGAGGACCCT CAGCTGCTGG AGGCCNCCCT | 540 |
| GGCCCAGCTG CCTCAGAGCC TGTCCTGCCT CCGCTCCGTG GTCCTCAAAG GGTCGATCTG | 600 |
| GGACCTCGGA CCCTGGCTCT GAGGGCCACA TCCGCCTCCC CCCTTCCCAG GAGGGCAACG | 660 |
| CCGGGACACA CTGGGTGCCT GTCTCCGGGG TGCCCTGACC AACCTGCCCG CTGGTCTGAG | 720 |
| TGGCCTGGCC CATCTGGCCC ACCTGGACCT GAGCTTCAAC AGCCTGGAGA CACTGCCGGC | 780 |
| CTGTGTCCTG CAGATGCGAG GTCTGGGTGC GCTCTTGCTG TCTCACAACT GCCTCTTTGA | 840 |
| GCTGCCTGAG GCTCTGGGGG CCCTCCCCGC CCTCACCTTC CTCATAGTGA CACACAACCG | 900 |
| CCTGCAGACG CTGCCCCCAG CACTGGGGGC CCTATCCACC CTGCAGCGCC TCGATCTCTC | 960 |
| TCAGAATCTG CTGGACACGC TACCTCCTGA GATTGGAGGC CTGGGCAGCC TCCTGGAGCT | 1020 |
| CAACCTGGCC | 1030 |

(2) INFORMATION FOR SEQ ID NO:12:

(i) SEQUENCE CHARACTERISTICS:

(A) LENGTH: 3205 base pairs
(B) TYPE: nucleic acid
(C) STRANDEDNESS: double
(D) TOPOLOGY: linear (ii) MOLECULE TYPE: cDNA (xi) SEQUENCE DESCRIPTION: SEQ ID NO:12:

```
GTCGACTCTC CTGCGTAGCC ATGGCGGTCC CATTCCCCAA CCCTCTTTCC AGTGGTGACC     60
CAAGCCTCCG GGGTTCAGGG TGACCACNAT GTCTCCCCCA CTCTGCATCC CAGGCCCATA    120
TGGCCTGGCT CTANAGCTCC CCACTCCATC CANAGTCCCC GTTTCCCCAA AGAGAANGGC    180
CCACCCCGGC TCCCGCTCAC TCCTCCTCCT GCCTCTGCAT CTTCCCCGGG CGCTGCCTGG    240
ACAGGCCTGC CTGCGTGCTG GGACATGTCT GGCCTCCAAG GACCGTCGGT GGGCGATGGC    300
TGCAACGGTG GAGGGGCCAG AGCTGGAGGC AGCTGCTGCC GCAGGAGATG CTTCAGAGGA    360
TTCGGACGCA GGGTCCAGGG CGCTTCCTTT CCTGGGCGGC AACCGGCTGA GCTTGGACCT    420
GTACCCCGGG GGCTGCCAGC AGCTGCTGCA CCTGTGTGTC CAGCAGCCTC TTCAGCTGCT    480
GCAGGTGGAA TTCTTGCGTC TGAGCACTCA CGAGGACCCT CAGCTGCTGG AGGCCNCCCT    540
GGCCCAGCTG CCTCAGAGCC TGTCCTGCCT CCGCTCCGTG GTCCTCAAAG GTCGATCTG     600
GGACCTCGGA CCCTGGCTCT GAGGGCCACA TCCGCCTCCC CCCTTCCCAG GAGGGCAACG    660
CCGGGACACA CTGGGTGCCT GTCTCCGGGG TGCCCTGACC AACCTGCCCG CTGGTCTGAG    720
TGGCCTGGCC CATCTGGCCC ACCTGGACCT GAGCTTCAAC AGCCTGGAGA CACTGCCGGC    780
CTGTGTCCTG CAGATGCGAG GTCTGGGTGC GCTCTTGCTG TCTCACAACT GCCTCTTTGA    840
GCTGCCTGAG GCTCTGGGGG CCCTCCCCGC CCTCACCTTC CTCATAGTGA CACACAACCG    900
CCTGCAGACG CTGCCCCCAG CACTGGGGGC CCTATCCACC CTGCAGCGCC TCGATCTCTC    960
TCAGAATCTG CTGGACACGC TACCTCCTGA GATTGGAGGC CTGGGCAGCC TCCTGGAGCT   1020
CAACCTGGCC TCCAACCGGC TGCAGAGCCT CCCAGCCTCT CTGGCGGGAC TTCGGTCCTT   1080
GCGGCTCCTT GTCCTGCACA GCAACCTCCT GGCCTCTGTG CCAGCTGACT TGGCCCGCCT   1140
TCCACTCCTC ACCCGGCTCG ACCTGAGGGA CAACCAGCTC CGGGACCTGC CCCTGAGCT    1200
GCTAGACGCC CCCTTTGTGC GCCTGCAGGG GAACCCCCTG GGTGAGGCCT CGCCAGACGC   1260
CCCGAGTTCA CCAGTGGCAG CCCTCATTCC AGAAATGCCC AGACTGTTCC TGACCTCAGA   1320
TTTGGACAGC TTTCCTGTGA CCCCTCGAGG CTGCTCAGTG ACCCTGGCCT GTGGCGTCCG   1380
CCTGCAGTTC CCAGCGGGAG CCACCGCCAC CCCCATCACC ATCCGCTATC GGCTGCTGCT   1440
GCCGGAGCCA GGCCTCGTCC CCTGGGTCC TCATGACGCC CTGCTCAGCC ATGTGCTGGA    1500
GCTGCAGCCC CATGGGGTGG CCTTCCAGCA GGATGTGGGG CTGTGGCTGC TCTTCACCCC   1560
ACCGCAGGCC CGGCGCTGCC GTGAAGTGGT GGTCAGGACC CGGAATGACA ACAGCTGGGG   1620
TGACCTGGAG ACCTACCTGG AGGAAGAGGC ACCCCAGCGG CTCTGGGCTC ACTGCCAGGT   1680
GCCCCACTTC TCCTGGTTCC TTGTGGTTTC CCGCCCTGTG TCCAATGCCT GCCTGGTGCC   1740
ACCGAGGGG ACACTGCTGT GCTCCTCGGG TCATCCTGGG GTCAAAGTCA TCTTCCCCCC   1800
TGGGGCCACT GAGGAGCCTC GTCGAGTCTC CATGCAGGTG GTGCGCATGG CTGGCCGAGA   1860
GCTGCAGGCC CTCCTGGGAG AACCAGAGGC TGCAGTGAGC CCCCTGCTGT GCCTGTCACA   1920
GAGCGGTCCC CCCAGCTTCC TCCAACCGGT CACCGTGCAG CTGCCTCTGC CCTCTGGCAT   1980
CACAGGCCTC AGTCTGGACC GCTCCCGCCT GCACCTGTTG TACTGGGCCC CTCCTGCAGC   2040
CACCTGGGAT GACATCACAG CTCAGGTGGT CCTGGAGCTC ACCCACCTGT ACTGGCTCTG   2100
```

```
GTACACCACC AAGAACTGTG TGGGAGGCCT GGCTCGGAAG GCCTGGGAGC GGCTGCGGCT      2160

GCACCGTGTG AACCTCATCG CTCTGCAGCG GCGCCGGGAC CCTGAGCAGG TCCTGCTGCA      2220

GTGCCTGCCC CGAAACAAGG TGGACGCCAC CCTTCGGCGG CTGCTGGAGC GGTACCGGGG      2280

CCCCGAGCCC TCTGACACGG TGGAGATGTT CGAGGGCGAA GAGTTCTTTG CGGCCTTCGA      2340

GCGCGGCATC GACGTGGATG CTGACCGCCC TGACTGTGTG GAGGGCAGAA TCTGCTTTGT      2400

CTTCTACTCG CACCTGAAGA ATGTGAAGGA GGTATACGTG ACCACCACTC TGGACCGGGA      2460

GGCTCAGGCT GTGCGGGGCC AGGTGTCCTT CTACCGTGGC GCGGTGCCTG TGCGGGTGCC      2520

CGAGGAGGCT GAGGCTGCCC GGCAGAGGAA GGGCGCAGAC GCCCTGTGGA TGGCCACTCT      2580

GCCCATCAAG CTGCCGAGAC TTCGAGGGTC CGAGGGGCCA CGGCGGGGGG CTGGCCTCTC      2640

CTTGGCACCC TTGAATCTGG GAGATGCCGA GACCGGCTTT CTGACGCAGA GCAACCTGCT      2700

GAGTGTGGCT GGGCGTCTGG GTCTGGACTG GCCAGCCGTG GCCCTGCACC TGGGGGTGTC      2760

CTACCGGGAG GTGCAGCGCA TCCGGCACGA GTTCCGGGAT GATCTGGATG AGCAGATCCG      2820

TCACATGCTC TTCTCCTGGG CTGAGCGCCA GGCTGGGCAG CCAGGGGCTG TGGGGCTCCT      2880

GGTGCAGGCC CTGGAGCAGA GTGACCGGCA GGACGTGGCT GAAGAGGTGC GCGCAGTCTT      2940

GGAGCTCGGC CGCCGCAAGT ACCAGGACAG CATCCGACGN ATGGGCTTGG CCCCCAAGGA      3000

CCCCGTTCTG CCTGGCTCCT CGGCTCCACA GCCCCCAGAG CCTGCCCAGG CATAGGCCCC      3060

ACAGAATTTT AGGCTGGCCC AGATATTCCC CAGTGGATGG GCAGAGCCCC CACCTTCAAG      3120

TCTCTCCAGT GTGTGGGGAC GGGTCCCTGT GAGCAACAAA ACTGCACTGT TTCTTTCACC      3180

TCGAAAAAAA AAAAAAAAAA AAAAA                                           3205

(2) INFORMATION FOR SEQ ID NO:13:

(i) SEQUENCE CHARACTERISTICS:
        (A) LENGTH: 753 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:13:

Met Arg Gly Leu Gly Ala Leu Leu Ser His Asn Cys Leu Phe Glu
1               5                   10                  15

Leu Pro Glu Ala Leu Gly Ala Leu Pro Ala Leu Thr Phe Leu Ile Val
            20                  25                  30

Thr His Asn Arg Leu Gln Thr Leu Pro Pro Ala Leu Gly Ala Leu Ser
        35                  40                  45

Thr Leu Gln Arg Leu Asp Leu Ser Gln Asn Leu Leu Asp Thr Leu Pro
    50                  55                  60

Pro Glu Ile Gly Gly Leu Gly Ser Leu Glu Leu Asn Leu Ala Ser
65                  70                  75                  80

Asn Arg Leu Gln Ser Leu Pro Ala Ser Leu Ala Gly Leu Arg Ser Leu
                85                  90                  95

Arg Leu Leu Val Leu His Ser Asn Leu Leu Ala Ser Val Pro Ala Asp
            100                 105                 110

Leu Ala Arg Leu Pro Leu Leu Thr Arg Leu Asp Leu Arg Asp Asn Gln
        115                 120                 125

Leu Arg Asp Leu Pro Pro Glu Leu Leu Asp Ala Pro Phe Val Arg Leu
    130                 135                 140

Gln Gly Asn Pro Leu Gly Glu Ala Ser Pro Asp Ala Pro Ser Ser Pro
```

-continued

```
            145                 150                 155                 160
Val Ala Ala Leu Ile Pro Glu Met Pro Arg Leu Phe Leu Thr Ser Asp
                165                 170                 175
Leu Asp Ser Phe Pro Val Thr Pro Arg Gly Cys Ser Val Thr Leu Ala
            180                 185                 190
Cys Gly Val Arg Leu Gln Phe Pro Ala Gly Ala Thr Ala Thr Pro Ile
            195                 200                 205
Thr Ile Arg Tyr Arg Leu Leu Leu Pro Glu Pro Gly Leu Val Pro Leu
210                 215                 220
Gly Pro His Asp Ala Leu Leu Ser His Val Leu Glu Leu Gln Pro His
225                 230                 235                 240
Gly Val Ala Phe Gln Gln Asp Val Gly Leu Trp Leu Leu Phe Thr Pro
                245                 250                 255
Pro Gln Ala Arg Arg Cys Arg Glu Val Val Arg Thr Arg Asn Asp
                260                 265                 270
Asn Ser Trp Gly Asp Leu Glu Thr Tyr Leu Glu Glu Ala Pro Gln
            275                 280                 285
Arg Leu Trp Ala His Cys Gln Val Pro His Phe Ser Trp Phe Leu Val
            290                 295                 300
Val Ser Arg Pro Val Ser Asn Ala Cys Leu Val Pro Pro Glu Gly Thr
305                 310                 315                 320
Leu Leu Cys Ser Ser Gly His Pro Gly Val Lys Val Ile Phe Pro Pro
                325                 330                 335
Gly Ala Thr Glu Glu Pro Arg Arg Val Ser Met Gln Val Val Arg Met
                340                 345                 350
Ala Gly Arg Glu Leu Gln Ala Leu Leu Gly Glu Pro Glu Ala Ala Val
            355                 360                 365
Ser Pro Leu Leu Cys Leu Ser Gln Ser Gly Pro Pro Ser Phe Leu Gln
            370                 375                 380
Pro Val Thr Val Gln Leu Pro Leu Pro Ser Gly Ile Thr Gly Leu Ser
385                 390                 395                 400
Leu Asp Arg Ser Arg Leu His Leu Leu Tyr Trp Ala Pro Pro Ala Ala
                405                 410                 415
Thr Trp Asp Asp Ile Thr Ala Gln Val Val Leu Glu Leu Thr His Leu
                420                 425                 430
Tyr Trp Leu Trp Tyr Thr Thr Lys Asn Cys Val Gly Gly Leu Ala Arg
            435                 440                 445
Lys Ala Trp Glu Arg Leu Arg Leu His Arg Val Asn Leu Ile Ala Leu
            450                 455                 460
Gln Arg Arg Arg Asp Pro Glu Gln Val Leu Leu Gln Cys Leu Pro Arg
465                 470                 475                 480
Asn Lys Val Asp Ala Thr Leu Arg Arg Leu Leu Glu Arg Tyr Arg Gly
                485                 490                 495
Pro Glu Pro Ser Asp Thr Val Glu Met Phe Glu Gly Glu Phe Phe
            500                 505                 510
Ala Ala Phe Glu Arg Gly Ile Asp Val Asp Ala Asp Arg Pro Asp Cys
            515                 520                 525
Val Glu Gly Arg Ile Cys Phe Val Phe Tyr Ser His Leu Lys Asn Val
            530                 535                 540
Lys Glu Val Tyr Val Thr Thr Thr Leu Asp Arg Glu Ala Gln Ala Val
545                 550                 555                 560
Arg Gly Gln Val Ser Phe Tyr Arg Gly Ala Val Pro Val Arg Val Pro
                565                 570                 575
```

-continued

```
Glu Glu Ala Glu Ala Ala Arg Gln Arg Lys Gly Ala Asp Ala Leu Trp
            580                 585                 590

Met Ala Thr Leu Pro Ile Lys Leu Pro Arg Leu Arg Gly Ser Glu Gly
            595                 600                 605

Pro Arg Arg Gly Ala Gly Leu Ser Leu Ala Pro Leu Asn Leu Gly Asp
            610                 615                 620

Ala Glu Thr Gly Phe Leu Thr Gln Ser Asn Leu Leu Ser Val Ala Gly
625                     630                 635                 640

Arg Leu Gly Leu Asp Trp Pro Ala Val Ala Leu His Leu Gly Val Ser
                645                 650                 655

Tyr Arg Glu Val Gln Arg Ile Arg His Glu Phe Arg Asp Asp Leu Asp
            660                 665                 670

Glu Gln Ile Arg His Met Leu Phe Ser Trp Ala Glu Arg Gln Ala Gly
            675                 680                 685

Gln Pro Gly Ala Val Gly Leu Leu Val Gln Ala Leu Glu Gln Ser Asp
            690                 695                 700

Arg Gln Asp Val Ala Glu Glu Val Arg Ala Val Leu Glu Leu Gly Arg
705                 710                 715                 720

Arg Lys Tyr Gln Asp Ser Ile Arg Arg Met Gly Leu Ala Pro Lys Asp
                725                 730                 735

Pro Val Leu Pro Gly Ser Ser Ala Pro Gln Pro Pro Glu Pro Ala Gln
            740                 745                 750

Ala
```